United States Patent [19]

Saklad

[11] 4,337,240
[45] * Jun. 29, 1982

[54] DENATURED ALBUMIN COMPLEXES FOR RADIOSCINTIGRAPHIC IMAGING AND EVALUATION OF RETICULOENDOTHELIAL SYSTEMS

[75] Inventor: Eugene L. Saklad, Sudbury, Mass.

[73] Assignee: New England Nuclear Corporation, Boston, Mass.

[*] Notice: The portion of the term of this patent subsequent to Oct. 7, 1997, has been disclaimed.

[21] Appl. No.: 18,312

[22] Filed: Mar. 7, 1979

Related U.S. Application Data

[63] Continuation-in-part of Ser. No. 898,292, Apr. 20, 1978, Pat. No. 4,226,846.

[51] Int. Cl.$^3$ ................ A61K 49/00; A61K 43/00; C07G 7/00
[52] U.S. Cl. ........................... 424/1; 260/112 R; 260/122; 424/1.5; 424/9
[58] Field of Search ................ 424/1, 1.5, 9; 260/122 R, 122

[56] References Cited

U.S. PATENT DOCUMENTS

| | | | |
|---|---|---|---|
| 3,720,761 | 3/1973 | Hunter | 424/1 |
| 3,863,004 | 1/1975 | Wolfangel | 424/1 |
| 4,032,625 | 6/1977 | Sobrramanian et al. | 424/1 |
| 4,071,613 | 1/1978 | Hunter | 424/1 |
| 4,094,965 | 6/1978 | Layne et al. | 424/1 |

FOREIGN PATENT DOCUMENTS 2424296 12/1974 Fed. Rep. of Germany .......... 424/1

OTHER PUBLICATIONS

Un et al., J. Nucl. Med., 13 (1972), 58–65; 928–931.
Honda et al., J. Nucl. Med., vol. 11, No. 10, 1970, pp. 580–585.
McCutcheons Detergents and Emulsifiers, North American Edition, (1973), pp. 213–217.
Wagner et al., J. Clin. Inv., 42:417 (1963).

*Primary Examiner*—Christine M. Nucker
*Attorney, Agent, or Firm*—Sewall P. Bronstein; George W. Neuner

[57] ABSTRACT

Small sized material (less than 0.2 μm, preferably less than 0.1 μm) comprising a complex of (1) denatured albumin, particularly human serum albumin and (2) a metal reducing agent, particularly a stannous reducing agent, preferably formed in the presence of a stabilizing ligand, which complex, when labelled with technetium-99m provides an excellent agent for imaging or otherwise evaluating reticuloendothelial systems (RES) and/or components thereof, particularly the bone marrow, liver and/or lymphatic system; methods of making and using the same; a complex (physical or chemical) of technetium-99m with such materials and methods of using such latter complex.

60 Claims, No Drawings

DENATURED ALBUMIN COMPLEXES FOR RADIOSCINTIGRAPHIC IMAGING AND EVALUATION OF RETICULOENDOTHELIAL SYSTEMS

This application is a continuation-in-part of application Ser. No. 898,292, filed Apr. 20, 1978, now U.S. Pat. No. 4,226,846, the disclosure of which is hereby incorporated by reference.

BACKGROUND OF THE INVENTION

The present invention relates to an agent for radioactively imaging or otherwise evaluating the reticuloendothelial system (RES) of vertebrates, especially primates, particularly the bone marrow, the liver, and the lymph nodes. Such agents are sometimes referred to as radioactive RES agents. More particularly the invention relates to an RES agent comprising an extremely small sized $^{99m}$Tc-labelled complex of a reducing metal and albumin (referred to hereinafter as a "minimicrocomplex"), particularly human serum albumin (HSA), to the unlabelled minimicrocomplex as such and in the form of a kit, to a method of making the same, and to methods of using the same for RES imaging and evaluation.

The reticuloendothelial system (RES) is a system comprised of most of the phagocytic cells in the body. These are cells which are able to dispose of foreign or other particles or cells by engulfing them, trapping them and/or metabolizing them. The RES includes the phagocytic cells which line the sinusoids of the liver (Kupffer cells), spleen, bone marrow, the lymphatic system, circulating macrophages, and phagocytic cells in certain other areas of the body. The organs of the RES have been effectively imaged with radiocolloids, which are taken up by the phagocytic cells. For example, RES agents injected into the blood stream are taken up and collected by the phagocytic cells in the RES, to give a latent radioactive image of the various components thereof, e.g., the liver, which can be converted into a visible image by appropriate instrumentation, e.g., by exposure of photographic film. Such images typically convey information about the size, shape, structure, location and/or condition of the various organs.

One area of particular importance in the field of pediatric health is bone marrow scintigraphy. Bone marrow imaging is indicated in both malignant and benign conditions. Many tumors, such as the neuroblastoma, metastasize to the bone marrow before there is involvement of the cortex of the bone. Similarly, leukemia and lymphoma may possibly be detected earlier by bone marrow imaging than by bone scanning. Eosinophilic granuloma primarily involves the bone marrow, and only later is the cortex of the bone affected. Infarction of bone is associated with decreased marrow activity, and thus bone marrow scintigraphy can also be useful in distinguishing infarction from the infection of bone.

Certain RES agents can be used to image the lymphatic system or portions thereof, more specifically either by direct injection into the lymphatic channels by interstitial injection (e.g., intramuscular, peri-prostatic), or by intraperitoneal injection, whereby the interstitial fluid and lymph carry the RES agent through the lymphatic system to various lymph nodes, where barring saturation and/or blockage of those lymph nodes in certain, typically metastatic, disease states they are requested by reticuloendothelial components of the nodes. By use of such RES agents, the lymph nodes in which such agents are collected can be imaged in a manner similar to the imaging of other organs. Radioscintigraphic imaging of the lymph nodes or other components of the lymphatic system is termed "lymphoscintography."

At one time the most common commercial RES imaging agent was a radiocolloid (particle size of 0.001–0.05 micrometers ($\mu$m)) of gold-198 ($^{198}$Au), stabilized with gelatin. However, these gold-198 imaging agents did not have the optimum physical characteristics for imaging, and gold-198 had an undesirably long half life, thus subjecting the RES and surrounding tissue to undesirably high dosages of radiation. Accordingly, with the advent of RES imaging agents utilizing the shorter half-life technetium-99m ($^{99m}$Tc), the use of the gold-198 agents has been almost completely supplanted.

One of the technetium-99m based RES agents is $^{99m}$Tc-labelled sulfur colloid-stabilized with gelatin, most of which has a particle size of $<0.1$–1.0 $\mu$m. This is presently still the most widely used radioactive RES imaging agent, despite a number of serious disadvantages, including: (a) requiring a relatively large number of components; (b) requiring boiling and neutralization steps for labelling by the user at the use situs, making the preparation of the agent for use both time consuming and cumbersome; and (c) not being biodegradable, and thus not being easily and quickly eliminated from the body. Following intravenous injection most of the sulfur colloid RES agents on the market do give sharp clear simultaneous images of the liver and spleen, although they are difficult to prepare. They are also used for imaging bone marrow. Although $^{99m}$Tc-labelled sulfur colloid is also used for imaging lymph nodes, the safety and efficacy of the available preparations are generally limited. When injected interstitially, most of the particles remain at the site of the interstitial injection, inflicting an undesirable radiation burden on that non-target tissue. Furthermore, it has been reported that when such particles are carried to lymph nodes, they seldom are carried beyond the first lymph node they encounter, even when that node is not otherwise obstructed. This makes it difficult to image a series or chain of lymph nodes, or to evaluate the extent to which lymph nodes in various locations have been obstructed as a result of a disease condition.

A $^{99m}$Tc-labelled stannous hydroxide colloid has also been marketed as an RES agent but it is a disadvantage in that it is difficult to prevent growth of the colloidal particles after labelling without the subsequent addition of stabilizers by the user at the use situs, which make them unsatisfactory for RES imaging; i.e., they are not stable.

Another RES agent which has been marketed in small quantities is a $^{99m}$Tc-labelled stannous phytate complex which, it is believed, is converted to an insoluble colloid by calcium in the bloodstream or lymph or interstitial fluid, from which it is then removed by the RES. However, with this agent, deficiencies have been found with respect to both retention at the injection site and uptake by the lymph nodes.

A $^{99m}$Tc-labelled antimony sulfide colloid has been reported as being commercially available certain countries, and is presently undergoing testing for use in the United States and Canada. While this material apparently does provide improved lymphoscintigraphic results as compared with the $^{99m}$Tc-labelled sulfur colloid and stannous phytate agents, it still suffers from the disadvantages that it is time consuming and difficult to prepare by the user, since preparation requires mixing with a stabilizer, boiling for a substantial time, cooling, buffering dilution to administration concentration, and pH testing, before use. Moreover, many of these steps must be taken with the radioactive material being outside of its shielded enclosure. Further, the antimony sulfide, like the sulfur colloid agent, is not biodegradable.

SUMMARY OF THE INVENTION

The present invention provides a highly stable biodegradable RES agent, which requires fewer components than the sulfur colloid RES agent, which does not require either a heating or neutralizing or any step by the user at the use situs other than addition of a $^{99m}$Tc pertechnetate solution, but yet which gives clinically useful images and evaluations of the RES and its constituent parts, particularly the bone marrow, the lymph nodes and the liver, and novel methods of making and using the same. The present invention also provides an RES agent which can be used to provide an evaluation of the overall or global function of the RES of a particular subject.

This is achieved by anaerobic denaturation of albumin, preferably human serum albumin (HSA), in the presence of a reducing metal in ionic or physical or chemical complex form (hereinafter referred to simply as reducing metal), preferably a stannous chloride, stannous iodide, stannous fluoride or stannous bromide, in such a manner as to form an albumin/reducing metal complex of extremely small size (preferably below 0.1 $\mu$m), which complex may then be labelled with $^{99m}$Tc by admixture with a radioactive pertechnetate solution and used directly, or may be freeze-dried and sealed in a sterile pyrogen-free vial and stored until ready for use. At the use situs, the minimicrocomplexes of the present invention are readily prepared for use. The minimicrocomplexes in solid form are subjected to a simple, short, vigorous mixture with a radioactive pertechnetate solution at the use situs.

The exact nature of the product of this invention is not presently known with certainty. The best denaturation process which is the preferred embodiment is similar to microaggregation processes previously used by the inventor to form microaggregated colloidal complexes of albumin and a reducing agent as described in copending U.S. application Ser. No. 898,292, filed Apr. 20, 1978, but with certain modifications of that process in order to produce particles of smaller size. Electron microscopy of products produced in accordance with the invention have shown the presence of very small microaggregates, the majority of which have a size of below 0.1 $\mu$m. Furthermore, a co-worker of the inventor, in analyzing a $^{99m}$Tc-labelled stannous denatured albumin complex product produced in accordance with this invention, discovered that it contained a substantial radioactivity associated with denatured material having a particle size approximately in the same range as the molecular size of undenatured albumin. Accordingly, it is believed that the reducing metal/albumin complexes which are the product of the present invention may contain a range of materials, from particles having a size comparable to the molecular size of undenatured albumin up to very small sized aggregates mostly less than 0.1 $\mu$m, of colloidal reducing metal/albumin complexes. The terms "minimicrocomplexes", "minimicroparticles" and "minimicroaggregates" as used herein are all intended to mean the very small complexes contained in the product of the present invention, regardless of whether such particles are made up of aggregates of smaller particles or are discrete single particles and regardless of whether the particles are of a particle size comparable to the molecular size of albumin, or are larger. Similarly, by "particle size" is meant the effective spherical diameter of the particle, regardless of whether or not the particle is in a molecular size range, or is a discrete particle or is an aggregate of a plurality of discrete particles.

Preferably the denaturation is also carried out in the presence of one or more additional ligands, preferably in a water soluble form, for stabilizing the reducing metal against precipitation before denaturation. Preferred ligands are the diphosphonates, preferably methylenediphosphonate, hydroxyethylenediphosphonate and aminoethanediphosphonate; and phosphates, such as the polyphosphates, e.g., pyrophosphates, the aminocarboxylates, such as diethylenetriaminepentaacetate salts; the polyhydroxycarboxylates such as glucoheptonate; and the polycarboxylates, such as the salts of carboxymethylcellulose. To date the diphosphonates have been found most preferable. However, other known physiologically and toxicologically compatible ligands for the particular reducing metal used are suitable. It has been found that the anion of certain useful reducing metal salts, such as stannous fluoride itself, has a sufficiently high stability constant to preclude the necessity of an additional ligand. In such case, the fluoride anion itself functions as a stabilizing ligand for the stannous ion.

It has been found that the minimicrocomplexes of the present invention provide RES agents which have substantial and surprising advantages over other RES agents which have been used in the past. These very small reducing agent/albumin complexes can be readily lyophilized and stored in the lyophilized state for months, and yet be quickly, almost instantaneously ready for use, simply by mixing the lyophilized material with an aqueous solution, preferably with the aqueous $^{99m}$Tc pertechnetate solution, e.g., obtained from a $^{99m}$Tc generator column which is used to label the minimicrocomplexes for radioscintigraphy. Thus the present invention obviates the exhaustive and time-consuming preparation processes required to be performed by the technician at the site of use in order to use the sulfur colloid agents and the antimony sulfide agents of the prior art. The product is useful for radioimaging a variety of the organs and cells of the RES, including a number of types of organs or cells which are difficult to image, e.g., the bone marrow, and the lymphatic system as well as other organs which are more easily imaged, such as the liver. In fact, in confidential preliminary studies on primates by an independent researcher, it was found that the labelled minimicrocomplexes of the present invention were far superior to the $^{99m}$Tc sulfur colloid which had previously been used for bone marrow scanning or imaging. It was reported that the present invention has about twice the activity uptake in bone marrow. See example IV, infra. This is particularly important, because with the sulfur colloid previously used, only a small fraction of the total activity localized in the bone marrow, resulting in long imaging times, and images of poor information density, thus limiting the usefulness of bone marrow imaging. Yet it is believed that at least in certain types of malignancies metastasizing cells migrate to the bone marrow prior to involvement of the cortex of the bone. Thus, while the use of bone scanning and imaging techniques has substantially reduced the time by which such metastases may be detected over that of previous X-ray techniques, the availability of a good radioscintigraphic agent for bone marrow may permit further reductions in time required for discovery of such metastases conditions.

The present invention is biodegradable, thus providing for rapid metabolic breakdown and removal from the patients' systems, whereas many prior art RES agents are not biodegradable.

The product also has utility in evaluating the reticuloendothelial system as a whole (sometimes referred to as a "global" RES function test), as opposed to individual evaluation of the various component parts of the RES. One of the neglected areas of clinical immunology research is the evaluation of the RES functional capacity in vivo. One method currently under investigation by medical researchers is a method to quantify measure the rate of clearance of particulate matter from the blood by the RES. See, e.g., Wagner, et al., "Studies of RES: I. Measurement of Phagocytic Capacity of RES in Man and Dog. J. Clinical Invest. 92:417 (1963), incorporated herein by reference. While, as pointed out above, various RES agents have been used to evaluate localization of particulate matter in various components of the RES, most previous agents were cleared so rapidly from the blood (half lifes for initial clearance of less than 1 minute), that use of such agents to study changes in blood clearance rates would be difficult. The minimicrocomplexes of this invention do not clear as quickly from the blood stream, having an initial half-life for blood clearance, for example, of about 4 minutes. Thus by injecting the material of the present invention into the bloodstream and evaluating the rate of disapperance of the radioactivity from the blood stream a measurement of the efficiency of the RES as a whole in removing particulate material can be obtained.

In accordance with the invention, radioactivity distribution by particle size of the labelled minimicrocomplexes indicates that at least a majority, preferably at least 75%, most preferably at least 90-94 percent of the activity is associated with complexes having a particle size of not more than 0.1 μm. Broadly, the particle size of the minimicrocomplexes of the present invention should be within the range of 0.004-0.2 μm, and preferably the size of the major part of the minimicrocomplexes is within the range of 0.01 to 0.08 μm. Most preferably substantially all, e.g., 85-95% of the complexes are within the range of about 0.01 to 0.08 μm. However, in certain uses of the product, e.g., liver imaging, somewhat larger particle sizes, e.g., about 0.05 to 0.2 μm may be useful.

Radioactivity distribution by particle size may be obtained by passing a known aliquot of a diluted suspension of the $^{99m}$Tc-labelled minimicrocomplexes through one or more polycarbonate filter membranes, e.g., membranes sold under the name NUCLEPORE by Nuclepore Corporation, assembled into NUCLEPORE filter housings according to the manufacturer's instructions and assembled in series in a stack of decreasing pore size (sometimes referred to as serial filtration technique) and then measuring the radioactivity of the filtered particles within each filter housing, and of the ultimate filtrate, by conventional measurement techniques, dividing each by the total radioactivity and multiplying by 100 to obtain the percentage. The aliquot is diluted sufficiently to prevent or minimize occluding of the pores of the filters which will reduce their effective size and thereby result in an incorrect measurement. A preferred technique for diluting the aliquot will be described hereinafter. All particle sizes referred to herein are particle sizes of products with which the activity is associated in the end use of the minimicrocomplexes. Preferably, when the minimicrocomplexes are subjected to $^{99m}$Tc-labelling, not greater than about 0 to 10%, more preferably not greater than about 3 to 5% of the activity travels to the solvent front on ITLC with methyl ethyl ketone (MEK). The ITLC is a mesurement of non-colloidally bound technetium, i.e. essentially free pertechnetate.

As noted above, for evaluation and visualization of the liver and bone marrow as well as for global RES function testing, $^{99m}$Tc-labelled minimicrocomplexes of reducing agent/denatured albumin, in aqueous media, are injected intravenously.

From less than 15 minutes to greater than 60 minutes after intravenous injection, excellent visualization of both the bone marrow and the liver are achieved with no significant non-target distribution at optimal acquisition for the respective target tissue. Marrow distribution, particularly in the vertebral and pelvic areas, can be imaged by acquisition for times beyond those which are optimal for liver, but not as long as have been required for imaging of bone marrow with colloidal sulfur RES agents, for example. This is because, as noted above, a larger proportion of the radioactivity associated with the reducing agent/denatured albumin complexes of the present invention localizes in the bone marrow than does the radioactivity associated with most previously used sulfur colloids.

When used for lymphoscintigraphy, the labelled product of the present invention is injected interstitially, as noted above, and tends to localize at first in lymph nodes through which the interstitial fluid passes in the region of the injection, and thereafter in lymph nodes farther removed from the injection site through which the lymph flows on its normal course toward the center of the body.

In preparing the products of the present invention, a solution of the albumin and reducing metal, preferably with an additional ligand in the solution, is denatured at a controlled pH, e.g., by heating at a suitable temperature to form the minimicrocomplexes.

The aforesaid particle size distribution is achieved primarily by controlling the concentrations of the components, the pH and the denaturation conditions as described more fully hereinafter.

The reducing metal becomes bound to the albumin (it is believed that a physical or chemical complex is formed) which increases the selective binding efficiency of the $^{99m}$Tc to the denatured minimicrocomplexes of reducing agent/denatured albumin when the minimicrocomplexes of reducing agent/denatured albumin are subsequently labelled, to thereby provide increased RES uptake and clear RES imaging.

The function of the additional ligand is to increase the amount of the reducing metal which can be stabilized against hydrolysis (formation of insoluble hydroxides or hydrated oxides of the reducing metal) before formation of the reducing metal/denatured albumin complexes. Without wishing to be bound by theory, it is believed that in the course of denaturation of the albumin caused by heating, conformational changes in the albumin expose reactive groups which enhance the affinity of the albumin for the reducing metal, thus binding substantially greater amounts of the reducing metal to and within the minimicrocomplexes than would otherwise be achieved in the absence of the additional ligand or as compared with reacting the reducing metal with the albumin after it has been denatured. In any event, the additional ligand contributes substantially to the excellent radioactive imaging of the RES. However, as aforesaid, when the anion of the water soluble reducing metal has a sufficiently high stability constant to stabilize the reducing metal against hydrolysis, as in the case of the fluoride, the need for an additional ligand may be obviated. In such cases the anion is in effect a stabilizing ligand for the reducing metal. As the skilled in the art will recognize, extremes of high or low pH should be avoided in order to further protect against other adverse reaction.

Where the minimicrocomplexes are to be freeze-dried for storage before use, they are preferably admixed before freeze-drying with a stabilizer solution of soluble undenatured albumin (HSA) to aid in the dispersion (reconstitution) of the solid freeze-dried particles in the pertechnetate solution when the latter is added thereto to label the minimicrocomplexes with $^{99m}Tc$ for use thereof. In a preferred embodiment, the stabilizer solution also contains a non-ionic surfactant (preferably Pluronic F-68) to further aid in the dispersion of the solid freeze-dried minimicrocomplexes in the pertechnetate solution.

Also, buffers, such as sodium phosphate, are added, preferably with the undenatured HSA and surfactant as part of the stabilizer solution, to achieve a pH sufficiently removed from the isoelective point of the reducing agent/denatured albumin complex to stabilize the reconstituted preparation against particle growth when the pertechnetate solution is subsequently added to the freeze-dried composition to form the $^{99m}Tc$-labelled albumin-$Sn^{++}$ minimicrocomplexes dispersed in saline or other pharmaceutically and pharmacologically acceptable carrier for injection into the patient. Therefore, when labelling a minimicrocomplexed product at a pH close to its isoelectric point it is advantageous to add such a buffered stabilizer solution in conjunction with labelling, even if the product is to be utilized without freeze-drying.

Among the most preferred ligands are the diphosphonates; of these methylene diphosphonate (MDP) and hydroxyethylene diphosphonate (HEDP) are preferred, but any of the diphosphonates described in U.S. Pat. No. 4,032,625 and German Offenlegungschrift No. 2,424,296 can be used.

Of the phosphates, pyrophosphate (preferably sodium pyrophosphate) is preferred. However, orthophosphate, the linear polyphosphates and organic phosphates, such as inositohexaphosphate may also be used.

Included among the aminocarboxylates which may be used are ethylenediaminetetraacetic acid (EDTA) salts and diethylenetriaminepentaacetic acid (DTPA) salts.

Although polyhydroxycarboxylates and polycarboxylates may function as weak ligands, they are not as preferable as those referred to above.

The stabilizing ligands which may be used are limited only by the ability to stabilize the reducing agent sufficiently against hydrolysis, and by toxicological considerations.

The most preferred albumin for human use is human serum albumin, although albumins from other species of animals, e.g., bovine serum albumin (BSA), may be used for diagnostic applications, particularly for those respective species. Delipidized albumin, as disclosed in U.S. Pat. No. 4,094,965, the disclosure of which is hereby incorporated by reference, is also suitable for use in the present invention. In many cases, HSA can be used in other species of animals without ill effects. However, the converse does not hold, e.g., BSA cannot be used in humans.

Any reducing agent can be used which is effective for reduction of the technetium-99m to an appropriate valence state for effective binding to the denatured albumin, without impairing the functional properties of the denatured albumin. Although the stannous ($Sn^{++}$) ion is preferred as a reducing metal, others such as the ferrous ($Fe^{++}$) ion, the monovalent copper ion ($Cu^+$), the titanous ($T^{+++}$) ion and/or the chromous ($Cr^{++}$) ion as well as some non-metal reducing agents can also be used. All these reducing agents can exist in at least two cationic redox states, of which a lower valence state is required for reduction of pertechnetate in subsequent labelling.

To form the product of the present invention, the albumin, in the presence of the reducing agent, preferably also in the presence of the stabilizing ligand, is denatured by suitable means, e.g., by heating of an aqueous solution thereof to a temperature between 70° C. and 100° C., more preferably 80°–100° C., and still more preferably between 85° C. and 99° C. Optimum results have been achieved with temperatures between 95° C. and 99° C. Higher temperatures can also be used, e.g., by increasing the pressure sufficiently to prevent substantial boiling of the reaction mass. Heating time may be between seconds and hours depending on the temperature and on the manner of heating. For example, heating by microwave energy or by radiofrequency heating or by induction heating requires only seconds whereas heating by immersion in boiling water or by passage through heating coils requires minutes. The maximum heating time is dictated by the fact that continued heating after formation of the minimicrocomplexes may increase the susceptibility of the $Sn^{++}$ to oxidation, or may degrade the reducing agent-/denatured albumin complexes. The minimum heating time and temperature are dictated by the time and temperature required to obtain the minimicrocomplexes of reducing agent/denatured albumin having particle size distribution desired as set forth above. The maximum heating time and temperature are dictated by the time and temperature beyond which degradation ensues. Using these guidelines, optimum heating temperature and time can easily be determined by routine testing of any given composition for any given manner of heating to provide the desired reducing agent/denatured albumin minimicrocomplexes described above. Excellent results have been achieved with heating times of 1 to 10 minutes at heating temperatures of 90°–99° C. where heating was carried out in a hot water bath, with acceptable results being achieved with heating times of 2–5 minutes using such a bath and temperatures. Most preferred is a time of 3–4 minutes at a temperature of 95°–99° C.

It is believed that the albumin becomes denatured during this heating step, i.e., denaturation occurs simultaneously with formation of the minimicrocomplexes of reducing agent/denatured albumin.

Other methods of denaturing the albumin are also suitable for use in the present invention, so long as the basic nature of the reducing agent/denatured albumin minimicrocomplexes are not adversely affected. Suitable methods include both mechanical methods, such as subjection of the albumin to high shear stress, high energy impact, high pressure, sudden substantial pressure drop ultrasonically, by solvent treatment or chemically, e.g., by subjection to agents which change the chemical structure of the albumin.

The denaturation is carried out at a pH sufficiently removed from the isoelectric point of the albumin (at which there is a 0 or near 0 charge on the molecules) to give the aforesaid particle size distribution. In this respect commercial HSA is comprised of a mixture of albumins with a distribution of isoelectric points. Consequently, the isoelectric points of the mixture may vary from lot to lot. They have been reported to range from pH 4.8 to 5.5; however, the presence of charged compounds which tend to associate with the albumin may shift its apparent isoelectric point significantly. They are believed to exert this effect, either by imparting their charge to the albumin or by neutralizing some positively or negatively charged groups on that protein.

The closer the pH is to the isoelectric point the larger the aggregate particles; thus at isoelectric pH macroaggregation or uncontrolled agglomeration occurs. As the pH is moved away from isoelectric pH toward the acid side or toward the alkaline side the particles become smaller and smaller. The optimum pH in the instant invention also varies somewhat depending on the additional ligand which is used. It has been found that the desired particle size distribution of the minimicrocomplexes can be achieved over a range of pH's, which again depends upon the particular additional ligand used, the most desirable ligand being that which provides the desired particle size over the widest pH range, thereby giving the least sensitive and most easily reproducible system. It has also been found that increasing ionic strength, e.g., by adding a neutral salt such as NaCl, during aggregation will shift the pH at which the desired particle size distribution is obtained further from the isoelectric point. Preferably, aside from the additional ligand and the reducing salt, the only other materials present which will affect the ionic strength of the denatured composition (the mixture which is subjected to denaturation) are the acid, e.g., HCl, or base, e.g, NaOH, used for pH adjustment. However, other materials which affect ionic strength may also be added, such as buffers or additional stabilizing ligands, which also show some buffering activity.

Although the desired particle size distribution can be achieved at a pH range on the acid side of the isoelectric pH and on the alkaline side, the latter is preferred since denaturation on the acid side presents other difficulties. Preferably the pH at denaturation differs from the isoelectric point by about 1.5 to 4 pH units, either on the acid side or on the alkaline side although more latitude exists on the alkaline side of the isoelectric point. More preferably, the pH at denaturation differs from the isoelectric point by about 2 to 3.5 pH units.

On the acid side of the isoelectric point the pH may range from about 1.0 to 4.5, preferably about 2.5 to 4.0 more preferably about 3.0 to 4.0. On the alkaline side of the isoelectric point it may range from about 6.5 to 11.0, more preferably between 7.5 and 9.5 and still more preferably between 8.0 and 9.0, depending upon the additional ligand and salts used and the concentrations of components.

The optimum pH for any particular ligand in any particular concentration can be determined by denaturing at different levels of pH away from the isoelectric point until the desired particle size distribution is achieved.

The reducing metal, e.g., stannous chloride, may be added to the albumin and ligand solution as a solid or it may be added as a solution.

The maximum amount of reducing metal is that beyond which precipitation thereof occurs before denaturation of the albumin. The minimum amount is that necessary to reduce and bind sufficient $^{99m}Tc$ to the denatured albumin to achieve clinically acceptable RES uptake. These amounts can readily be determined for particular admixtures by routine experiment. Very small amounts of reducing metal are effective for adequate reducing and binding of the $^{99m}Tc$ to the denatured albumin, e.g., less than an 8:1 molar ratio of stannous to albumin, but because it is easily oxidized, compositions using the minimum amount required may lose their effectiveness over a period of time after storage, handling or use. Accordingly, an excess over the minimum amount for adequate binding of the $^{99m}Tc$ is preferably used. As the amount of reducing metal is increased, there appears to be a point for any given combination of starting compounds at which binding effectiveness of the $^{99m}Tc$ to the albumin no longer increases either initially or as a function of time up to 24 hours or more after labelling.

Keeping this in mind, the molar ratio of reducing metal, particularly $Sn^{++}$, to albumin may vary over a wide range, i.e., from 8:1 to 200:1, preferably 30:1 to 80:1. It is preferred that the molar ratio of $Sn^{++}$ to albumin not exceed 100:1. Excellent results have been achieved with molar ratios of $Sn^{++}$ to albumin of from about 30:1 to 50:1.

The minimum amount of additional ligand is that required to avoid the formation of any substantial amounts of the insoluble hydroxide or hydrated oxide of the reducing metal for any given composition by binding the reducing metal. The maximum amount is that beyond which it commences to compete substantially with the albumin for the $^{99m}Tc$ when the minimicrocomplexes are admixed with the pertechnetate. Such ligands, when present in excess of that required to stabilize the reducing metal, particularly those with high affinity for Tc, may react with the $^{99m}Tc$ to form complexes which seek bone, kidney, or other non-target tissues, thereby increasing non-target uptake at the expense of RES uptake and reducing the effectiveness of the reducing agent/denatured albumin minimicrocomplexes as RES agents. Accordingly, the amount of ligand should not be in substantial excess of that amount which is required to stabilize the reducing metal. The minimum and maximum amounts of ligand can be easily determined by routine testing for insoluble hydroxides before aggregation and by observing the effect on bone uptake, kidney uptake, urinary excretion, and other non-target distribution by the denatured product. Furthermore, the greater the concentration of ligand the narrower may be the pH range over which the desired particle size distribution is achieved during denaturation. Accordingly, for optimum results it is desirable to use little more than the minimum amount of ligand necessary to maintain the reducing metal in solution before aggregation.

The concentration of additional ligand and the maximum and minimum amounts thereof also depends upon the ligand used, since some ligands, such as MDP, have a greater binding capacity (higher stability constant)

and a lesser ionic strength than other. A ligand which provides the widest range of pH's over which the desired particle size distribution is achieved is the most desirable. The diphosphonates, particularly MDP and HEDP, fall in that category. The maximum and minimum amounts of ligand also depends on the particular pH at which the denaturation is carried out.

The optimal amount of additional ligand is too small to have any appreciable buffering effect or to appreciably reduce the target to non-target activity ratio even though the ligand may be one which is known to seek non-target tissues. It is interesting to note that the addition of ligand which is known to seek non-target tissues, enhances the target to non-target ratio.

Since it is the complexing moiety of the ligand which functions to bind the reducing metal, the concentration of ligand is best expressed as a molar ratio of such moiety to reducing metal ion, e.g., $Sn^{++}$. This ratio is strongly dependent upon the choice of ligand as well as on the pH. For one such as methylene diphosphonate, which has a fairly high stability constant, such ratio is preferably between 0.6:1 and 1.2:1; for one such as glucoheptonate, which has a fairly low stability constant, about 2½ times that ratio is preferred.

Using MDP and stannous chloride and a pH range of 8.0 to 9.0 successful results have been achieved with a ligand:$SnCl_2.2H_2O$ weight ratio of about 0.75:1. If the pH is increased beyond this range the concentration of MDP may have to be increased to achieve the same biodistribution.

It is clear from the above that there is a functional interdependence between the choice and concentration of ligand and the optimal pH for obtaining complexes of the proper size range during denaturation.

In a preferred embodiment of the invention the denaturation is carried out in the presence of a water soluble, pharmacologically and toxicologically acceptable surfactant of the same type which is preferably included in the stabilizer solution. Although good results have been achieved without the presence of a surfactant during denaturation it is preferred to use it as an additional safeguard since it is believed it may increase the reproducibility and stability of the minimicrocomplexes, and may aid in their redispersion in the correct particle size range when lyophilized reducing agent/denatured albumin complexes are reconstituted and labelled for use.

A wide variety of surfactants is suitable for use in the denaturation step and in the stabilizer solution. Preferably the surfactants are of the non-ionic type and are solids at room temperature. The useful surfactants are those which are non-toxic to blood components or tissues and preferably have a hydrophilic/lipophilic balance (HLB) of about 14 to about 40, more preferably about 27–30.5. When a surfactant is used in the denaturation step only a very small amount is usually used, e.g. an amount by weight of about 0.1% to about 10% of the albumin being denatured, preferably about 2–8% by weight.

The surfactant dissolved in the stabilizer solution, as aforesaid, aids in the rapid dispersion (reconstitution) of the freeze dried reducing metal/denatured albumin minimicrocomplexes in the pertechnetate solution when the latter solution is added thereto for administering to the patient. The amount of surfactant used in the stabilizer solution is usually much greater than the amount used in the denaturation step.

Preferably the surfactant in the stabilizer solution is present in an amount of about 0.2% to 20%, more preferably 1 to 10% of the lyophilized composition (solid basis).

Suitable surfactants for use during aggregation and in the stabilizer solution include Polysorbate 80, U.S.P., higher molecular weight polyethylene glycols such as Carbowaxes made by Union Carbide; and molecular combinations of polyoxethylene and polyoxypropylene (ethylene oxide-propylene oxide block copolymers), e.g., the Pluronics, made by BASF Wyandotte. See also, McCutcheon's *Detergents and Emulsifiers*, North American Edition (1973) at pages 213–217, where many commercially available surfactants having HLB numbers between about 14 and 40 are listed. Most preferred are the Pluronics, particularly Pluronic F-68, which has a molecular weight of about 8350, an HLB No. of 29.0 and is a solid at room temperature.

The volume ratio of denatured albumin stabilizer solution (containing surfactants and buffers when they are used) added to the aqueous product containing the reducing agent/denatured albumin minimicrocomplexes prior to lyophilization may vary over a wide range. Suitable ratios include from about 1:1 to 1:3, with a ratio of 1:2 being preferred.

Based on the final lyophilized solid composition the ratio of undenatured albumin to denatured albumin may range from about 3:1 to 20:1, more preferably 5:1 to 15:1.

A buffering compound may be added to the aqueous denatured product either as part of the stabilizer solution, or, when such solution is not used, directly, to maintain the pH far enough from the isoelectric point to stabilize it against particle growth during or after lyophilization or labeling. Any compatible pharmacologically and toxicologically acceptable buffer compound can be used which does not compete significantly for the $^{99m}Tc$. Suitable buffers are well known, and include mixtures of acids and salts of weak acids, such as the appropriate sodium salts of orthophosphoric acid.

In some instances, it may be desirable to add an electrolyte to the aqueous denatured product, such as alkali or alkaline earth metal soluble salts, e.g., NaCl, for adjustment of ionic strength.

The maximum amount of $^{99m}Tc$ (pertechnetate) added to the lyophilized product relative to the denatured albumin is dictated by the fact that any substantial excess over that which becomes bound to the minimicrocomplexes has no beneficial effect and should be avoided for reasons having nothing to do with the invention: namely because the amount of radioactive material injected into the body should be kept to the minimum required. However, a slight excess over that which becomes bound to the minimicrocomplexes may be used. Based upon primate studies, up to 10% free pertechnetate would probably not impair clinical utility. The minimum amount is dictated by that amount required to give clinically acceptable images. The molar ratio of $^{99m}Tc$ to denatured albumin (based on molecular weight of the albumin before denaturation) may be as great as 0.25 or greater.

The radioactive dosage of the $^{99m}Tc$ labelled minimicrocomplexes of the invention may vary from 0.01 to 50 mCi (millicuries) per patient, depending upon patient weight and type of testing being done, but preferably is from 0.1 to 8 mCi.

Preferably, the volume of the pertechnetate solution added to the aqueous denatured product as such, or after freeze drying, may vary from 1–10, preferably 1–8, ml containing 1–300 or more, preferably 50–150, mCi per milligram of denatured albumin. The pertechnetate solution is usually the eluate from a conventional $^{99m}$Tc generator but it need not be.

Better binding of the reducing metal to the denatured albumin and more homogeneous minimicrocomplexes are achieved with less oxidation of the reducing metal by admixing it and the additional ligand with the albumin before denaturation, with resulting improved RES imaging. Without wishing to be bound by theory, it is believed that more intimate contact between the albumin and reducing metal is achieved because, as the albumin opens up during heating, the freshly exposed binding sites thereof react with the reducing metal before and during denaturation and the reducing metal becomes an intimate part of the minimicrocomplexes.

In any event, it has been found that better results are achieved when the albumin is denatured in the presence of the reducing metal. However, the presence of the reducing metal during denaturation presents problems which are not present when albumin is denatured without the presence of the reducing metal. One such problem is to achieve the particle size distribution desired; another is the binding of the required amount of reducing metal to the denatured albumin; another is to avoid the formation of insoluble reducing metal hydroxides or hydrated oxides. These problems are overcome by the presence of the ligand during denaturation, by control of pH and heating conditions during denaturation, and by maintaining anaerobic conditions throughout.

The water or other pharmaceutically acceptable carrier used to form the various solutions and/or suspensions in which denaturation and further processing occurs is preferably nonpyrogenic distilled water which has been treated to reduce the oxygen contained therein.

Also, preferably all the steps of the process are carried out under anaerobic conditions, i.e., in the absence of oxygen, as for example under a nitrogen atmosphere.

In the preferred embodiment the mixture of stabilizer solution and reducing metal/denatured albumin minimicrocomplexes, containing the ligand, when one is used, are freeze-dried in conventional manner in sterile nonpyrogenic containers or vials which are sealed and marketed in the form of a kit which can be used at the use situs by adding the prescribed amount of radioactive pertechnetate to the vial.

With respect to the technique for determining the radioactivity distribution of the minimicrocomplexes by particle size, an appropriate technique which has been used for diluting the aliquots of $^{99m}$Tc labelled minimicrocomplexes for passage through the filters arranged in series is by adding to the product resulting from the addition of the pertechnetate solution to the minimicrocomplexes (i.e., the labelled product), a dilution of the stabilizer solution in a volume ratio of 9 parts diluted stabilizer solution to 1 part of labelled complexes. This ratio may vary over a wide range so long as the finally diluted aliquot does not unduly occlude the pores of the filter membranes. The diluted stabilizer solution is prepared by adding a sufficient amount of saline solution thereto to dilute it to about the same solids concentration as that of th labelled product. The particle size distributions referred to herein were obtained by this technique. However, other techniques can be used.

Although the stabilizer solution is not required when the reducing metal/denatured albumin complexes are to be used without freeze-drying (in such case the buffer can be added as such), it is nevertheless preferred to add the stabilizer solution with the buffer, to stabilize the particle size upon addition of the pertechnetate solution, especially for compositions which are denatured relatively close to the isoelectric point. As indicated above, the minimicrocomplexes may be labeled and used as an RES agent directly after denaturation, although such products are normally lyophilized preferably after addition of the stabilizer solution. The unlyophilized product can normally be used for about one day or more. Lyophilization provides a product which can be stored for six months or more before use and can readily be reconstituted. Upon reconstitution, the lyophilized product does not differ substantially from the unlyophilized product, although there may be minor variations, e.g., in particle size, which would not produce a significant difference in most cases. Minor variations, e.g., in particle size may have some significance in cases where use of the product is highly sensitive to particle size variations. Conditions which are known to have the potential of degrading proteins, such as extremes of temperature, exposure to light, contamination, etc. should, of course, be avoided both for the lyophilized and unlyophilized products.

The process of the invention can be carried out as a batch process, a semi-continuous process or a continuous process.

Preferably prior to denaturation, the aqueous material containing the undenatured albumin, the reducing agent, the ligand, and possibly other materials, is filtered through a sterilizing membrane, e.g., an 0.22 μm sterilizing membrane, and the stabilizer solution is filtered through a sterilizing filter before being added to the denatured product.

To the naked eye, the denatured product having the preferred particle size range is comparable in clarity to the composition before denaturation. Haziness indicates the likely presence of particles which are larger than the preferred particle size. A milky appearance is especially undesirable. Thus the product should be checked for appearance after the denaturation step and at other times, e.g., after the reconstitution of the lyophilized product.

EXAMPLE 1—DENATURATION

To 90 ml of mixing low oxygen water the following are is added anaerobically: 0.6 ml Human Serum Albumin, 25% (25 g/100 ml), Salt Poor, U.S.P., the HSA weighing 0.15 grams, 3 ml sodium methylene diphosphonate (MDP) solution (0.5 grams methylene diphosphonic acid dissolved in 100 ml 0.05 N sodium hydroxide. To this composition the following are added with constant stirring: sufficient 0.05 N sodium hydroxide to adjust the pH to about 7.8; 0.5 ml of stannous chloride solution (4.2 grams stannous chloride dihydrate plus 1.5 ml 12 N hydrochloric acid diluted to 100 ml with low oxygen water); and 0.6 ml of a 1% aqueous solution of Pluronic F-68, an ethylene oxide propylene oxide block copolymer nonionic surfactant. The solution is titrated with 0.05 N sodium hydroxide until the pH is 5.8. Aliquots of this solution, filtered anaerobically through an 0.22 μm sterilizing membrane and heated for 3.5 minutes in a water bath at about 99° C., yield milky suspensions of microaggregates of the denatured albumin and $Sn^{++}$.

Portions of the remaining undenatured bulk solution are titrated to pH's of from about 6.2 to 9.5 by addition of 0.05 N sodium hydroxide solution. Aliquots of these clear solutions, filtered anaerobically through an 0.22

μm sterilizing membrane and heated for about 3.5 minutes at about 99° C., yield compositions of stannous-/denatured albumin having the following physical appearance as tabulated in Table I:

TABLE I

Effect of pH on Appearance After Denaturation

| No. | pH* | Appearance after denaturation |
|---|---|---|
| 1 | 5.8 | milky |
| 2 | 6.2 | light milky to very cloudy |
| 3 | 6.4 | hazy |
| 4 | 6.6 | nearly clear |
| 5 | 7.0 | clear |
| 6 | 7.5 | clear |
| 7 | 7.6 | clear |
| 8 | 7.9 | clear |
| 9 | 8.1 | clear |
| 10 | 8.5 | clear |
| 11 | 8.8 | clear |
| 12 | 9.2 | clear |
| 13 | 9.5 | clear |
| 14 | 10.5 | clear |

*As is known in the art, the measurement of pH of protein solutions, especially at low ionic strength, is difficult, and some variations occur. Thus while these pH measurements were very carefully measured, they should probably be considered as being accurate within ± 0.2 pH units.

EXAMPLE 2—STABILIZATION AND LABELLING

To approximately 50 ml of low oxygen water are added anaerobically 5.7 grams disodium orthophosphate heptahydrate (buffer), 12 ml of 25% HSA (i.e., undenatured) and 0.33 grams of Pluronic F-68. After dissolving the solids, the stabilizer solution is diluted to 100 ml with low oxygen water and is passed through a sterilizing filter anaerobically.

3.3 ml portions of the above sterile stabilizing solution are mixed anaerobically with 6.7 ml of each of the sterile stannous/denatured albumin compositions designated as Nos. 4, 5, 7, 8, 10, 11 and 13 in Example 1. 1 ml aliquots of these formulations, which have pH's of about 6.6 to 9.5, are dispensed aseptically into sterile non-pyrogenic 10 ml serum vials. The vials are freeze-dried (lyophilized) in a conventional manner and under aseptic conditions to remove water. This provides solid microaggregates or minimicroparticles of the complex (chemical or physical) of denatured albumin and $Sn^{++}$. Each vial contains about 1 milligram of particles of complexed denatured albumin, 10 milligrams of undenatured HSA, 0.1 milligrams of $SnCl_2$, 0.1 milligrams of MDP, 10 milligrams of phosphate buffer (expressed as disodium orthophosphate) and 1.14 milligrams of Pluronic F-68 surfactant.

The vials are septum-sealed and stored until ready for use, at which time the stannous denatured albumin contained therein is labelled with $^{99m}Tc$.

To prepare the $^{99m}Tc$-labelled products, five milliliters of fresh radioactive sodium pertechnetate (about 100 mCi, although effective labelling is obtained from less than 1 mCi to greater than 300 mCi), are removed as a sterile non-pyrogenic eluate from a sterile NEN $^{99m}Tc$ generator in an 0.9% saline solution, and added aseptically to each vial. The vial is shaken to dissolve the soluble components and disperse the colloidal particles in the saline solution, thereby reconstituting the freeze-dried product and labelling the stannous-/denatured albumin complexes.

Aseptic techniques and sterile, non-pyrogenic ingredients and containers are used at all steps.

Activity distribution by particle size of the samples revealed the following for such preparations:

TABLE II

| | PERCENT OF TOTAL RADIOACTIVITY | | | | | | |
|---|---|---|---|---|---|---|---|
| Sample No. | 4 | 5 | 7 | 8 | 10 | 11 | 13 |
| Pre-denaturation pH | 6.6 | 7.0 | 7.6 | 7.9 | 8.5 | 8.8 | 9.5 |
| Particle size | | | | | | | |
| ≧0.2 μm | 67 | 24 | 3 | 2 | 3 | 2 | 4 |
| 0.1–0.2 μm | 6 | 8 | 3 | 2 | 2 | 1 | 2 |
| <0.1 μm | 27 | 68 | 94 | 96 | 95 | 97 | 94 |
| (<0.08 μm)* | | | | (94) | | (95) | |

*Data available only for samples 8 and 11

EXAMPLE 3—BIODISTRIBUTION IN MICE

1–5 mCi of each of these preparations of $^{99m}Tc$ labelled stannous denatured albumin complexes was injected into adult mice intravenously. Fifteen minutes after injection the mice were sacrificed, and the various organs (liver, spleen, etc.) were counted by conventional gamma ray counting techniques to determine uptake of $^{99m}Tc$ by each organ.

Biodistribution in the mice 15 minutes after intravenous injection was as follows:

TABLE III

| | PERCENT OF INJECTED DOSE PER ORGAN | | | | | | | | |
|---|---|---|---|---|---|---|---|---|---|
| Sample No. | 4 | 5 | 6 | 7 | 8 | 9 | 10 | 11 | 12 | 13 |
| Organ | | | | | | | | | | |
| Liver & Spleen | 85 | 89 | 86 | 88 | 75 | 80 | 76 | 77 | 73 | 76 |
| Lungs | 2 | <1 | 1 | <1 | 2 | 1 | 2 | 2 | 2 | 2 |
| Carcass (incl. bone marrow) | 8 | 8 | 10 | 7 | 16 | 13 | 13 | 15 | 14 | 12 |
| Kidneys | 2 | 1 | 1 | 1 | 2 | 2 | 2 | 2 | 3 | 2 |
| Gi tract | 1 | 1 | <1 | 1 | 1 | 1 | 1 | 1 | 1 | 1 |
| Blood | 1 | 1 | 1 | 1 | 5 | 3 | 6 | 5 | 5 | 5 |
| Urine | 3 | 2 | <1 | 1 | 2 | <1 | 1 | 1 | <1 | 1 |

Thus it is evident that with decreasing particle size there is a trend toward increasing the retention of the radioactivity by the carcass, with corresponding decreased localization in the liver and spleen. This information, together with studies in rabbits, which indicated that over 95% of the radioactivity localized in bone by use of an RES agent in accordance with the present invention was localized in the bone marrow, as opposed to the hollow bone shaft, suggested that the RES agents of the present invention might be advantageous as bone marrow imaging agents. This was confirmed in the experiments with primates described in Example 4.

EXAMPLE 4—BONE MARROW IMAGING IN PRIMATES

The use of the minimicrocomplexes of the present invention for bone marrow imaging in primates is illustrated by using such materials for imaging bone marrow in each of two female baboons. The results of such use are compared with other RES imaging agents.

Two lots of the stannous/denatured human serum albumin of the present invention are prepared in the manner described in Examples 1–3, with the pre-denatured pH adjusted to about 8.5. A semi-continuous process is utilized for heating Lot 1. After the admixture of HSA, methylene diphosphonate, stannous chloride, and Pluronic F-68, the composition, at a pH of about 8.5, is sequentially and continuously run through two heat exchangers, designed and controlled to expose the admixture to a temperature of about 95° C. for a bulk average residence time of about 3.5 minutes and to restore the hot reaction mixture to ambient temperature. This provides a semi-continuous method for denaturation which can be made fully continuous by use of metered and continuous flow of the compounding materials into a mixing chamber, with flow therefrom through the filter and heat exchangers, with the exit from the heat exchangers being metered into a mixing chamber into which the stabilizer solution is metered and mixed, with the resulting mixture being dispensed into vials, which may be loaded into the freeze dryer, all steps in the process being performed continuously.

The compositions containing the stannous/denatured albumin minimicrocomplexes are both clear. These preparations are labelled with $^{99m}$Tc in the manner described in Example 2. The radioactivity distribution by particle size for Lot 2 indicates that about 98% of the activity is bound to minimicrocomplexes having a particle size of less than 0.08 μm. Biodistribution of the material of Lot 2, run in a manner similar to that described in Example 3, gave percentages of injected dose of about 82 for liver and spleen, 1 for lungs, 12 for carcass, 2 for kidneys, 1 for GI tract, 8.5 for blood, and <1 for urine. Lot 2 was made in the batch process generally described in Example 1, and had similar biodistribution data of about 82 for liver and spleen, 1 for lungs, 12 for carcass, 1 for kidneys, 1 for GI tract, 6 for blood, and 1 for urine. About 94% of the activity of Lot 2 was associated with minimicrocomplexes smaller than 0.08 μm.

Lots 1 and 2 of the material were compared with other RES imaging agents, including those based on $^{99m}$Tc-labelled sulfur colloid, stannous microaggregated albumin, as described in copending U.S. application Ser. No. 898,292, filed Apr. 20, 1978, colloidal antimony sulfide, and stannous phytate. After labelling with $^{99m}$Tc in accordance with manufacturers instructions, the imaging agents listed in the table below were injected intravenously into two female baboons ("A" and "B") at a dosage level of approximately 80 μCi/kg of body weight. Images were obtained in the posterior projection, including the liver, spleen and lower spine. The initial images were at 20 minutes post-injection, and subsequent images were taken at about one hour. For each agent, the contrast ratios reported in Table IV were calculated by dividing the average intensity of radiation per unit area in the marrow by the average intensity per unit area in the liver, both figures being corrected for background radiation.

TABLE IV

RATIOS OF AVERAGE INTENSITY PER UNIT AREA IN THE MARROW TO THAT IN THE LIVER

| AGENT | ANIMAL | IMAGING TIME (min.) POST-INJECTION | |
|---|---|---|---|
| | | 20 | 60 |
| Stannous Minimicrocomplex of Albumin | | | |
| Lot 1 | A | .08 | .07 |
| | B | .09 | .09 |
| Lot 2 | A | .09 | .09 |
| Sulfur Colloid | A | .05 | .05 |
| | B | .06 | .06 |
| Stannous Microaggregated Albumin | A | .04 | .05 |
| | B | .05 | .05 |
| Colloidal Antimony Sulfide | | | |
| Preparation 1 | A | .05 | .05 |
| | B | .04 | .03 |
| Preparation 2 | A | .04 | .04 |
| | B | .06 | .04 |
| Stannous Phytate | A | .03 | .02 |
| | B | not tested | .02 |

It is readily apparent that the ratios of average intensity per unit area in the marrow to that in the liver for the $^{99m}$Tc-labelled stannous minimicrocomplexed albumin are significantly greater than those of all the other RES agents with which they were compared. The results listed in Table IV were obtained on a confidential basis by the Harvard Medical School, Children's Hospital Medical Center, of Boston, Mass., an organization which is totally independent of the inventor and the owner of this application. The investigators who obtained the data concluded:

Using the usual sulfur colloid preparation as a standard, it was found that the [minimicrocomplex of the present invention] resulted in almost twice as much activity in the bone marrow. The liver/marrow and spleen/marrow ratios were also lower, reflecting the more favorable bone marrow uptake In conclusion, the most promising of the agents investigated for bone marrow was the [minimicrocomplex of] albumin.

EXAMPLE V—USE AS LYMPHOSCINTIGRAPHIC AGENT

Following intramuscular (interstitial) injection subcostally in either rabbits or baboons, Lot 1 of example IV and preparations similar to Lot 2 of that example were found to be useful for imaging lymph nodes, when compared with $^{99m}$Tc-labelled antimony sulfide. $^{99m}$Tc-labelled sulfur colloid and stannous microaggregated albumin were both less suitable because so much activity remained at the injection site. $^{99m}$Tc-labelled stannous phytate was unsuitable because it diffused so readily into the blood, from which it distributed rapidly to liver, kidneys, and bladder.

Following peri-prostatic injection, regional lymph nodes may also be imaged.

EXAMPLE VI—USE AS AGENT FOR MEASURING GLOBAL RES FUNCTION

Data on blood clearance in mice of a $^{99m}$Tc-labelled vial from Lot 1 of example IV are tabulated below, along with comparable data on a vial of stannous microaggregated albumin, prepared in accord with the specification of copending application Ser. No. 898,292, filed Apr. 20, 1978. The much slower initial blood clearance of the minimicrocomplexes is readily apparent, all but 3% of the radioactivity injected with the microaggregates having been cleared from the blood in the first 5 minutes. Radioactivity bound to the minimicrocomplexes was not cleared to the same level until about 30 minutes after injection. Clearly, the initial blood clearance of the minimicrocomplex would be slow enough to provide a sensitive index of global RES function.

| Time (min) post-injection | % of Injected Radioactivity in Blood | |
|---|---|---|
| | Minimicro-complex | Microaggregated Albumin |
| 5 | 17 | 3 |
| 15 | 8 | 3 |
| 30 | 3 | 2 |

EXAMPLE VII

To a portion of a "pre-aggregation bulk" prepared as for Example 6 in copending application Ser. No. 898,292, filed April 20, 1978 (based upon HSA delipidized by acidification and activated charcoal in accord with U.S. Pat. No. 4,094,965 followed by ultrafiltration, and utilizing pyrophosphate as the stabilizing ligand), sufficient 0.025 N sodium hydroxide is added, with continuous mixing, to adjust to pH 6.4 The remaining portions are adjusted to pH's of from about 6.5 to 6.9 in similar fashion. Aliquots of these clear solutions, each filtered anaerobically through an 0.22 μm sterilizing membrane and heated for about 3.5 minutes at about 99° C., yield compositions of stannous/denatured albumin of which all but the first remain clear, that at pH 6.4 turning slightly hazy. Formulated with stabilizer solution and labelled with $^{99m}$Tc, both as in Example 2 above, activity distribution by particle size on the slightly hazy sample shows at least 92% of the radioactivity associated with material less than 0.2 μm, with less than 1% unbound technetium. Thus the particle size of this product is clearly smaller than that of Example 2 (pH 7.0, 76% less than 0.2 μm). Biodistribution is similar to that of Sample No. 5 of Example 3 above, giving percentages of injected dose of 88 for liver and spleen, 1 for lungs, 9 for carcass, 1 for kidney, <1 for GI tract, <1 for blood and <1 for urine.

It is evident from the similarity of the test data, despite significant differences in pH before denaturation, that a choice of stabilizing ligand may be made which permits the use of different pH's to obtain the same particle size range. This ability to vary the pre-denaturation pH used to obtain a particular desired particle size range of minimicrocomplex can be put to advantage, e.g., by choosing a ligand which permits the use of lower pH's to obtain the desired particle size, it being easier to stabilize some reducing agents at lower pH's. Similarities and differences are demonstrable for a wide variety of other useful stabilizing ligands, including orthophosphate, hydroxyethylene diphosphonate, glucoheptonate, and diethylenetriaminepentaacetate.

I claim:

1. A composition for labelling with $^{99m}$Tc for radioactive imaging comprising complexes of denatured albumin and a reducing metal, at least a major portion of which having a particle size of less than about 0.2 μm.

2. A composition according to claim 1, said composition also comprising an additional stabilizing ligand for said reducing metal.

3. A composition according to claim 2, said ligand being selected from the group consisting of a phosphonate, a phosphate, an aminocarboxylate, a polyhydroxycarboxylate and a polycarboxylate.

4. A composition according to claim 3, said reducing metal comprising a stannous reducing metal.

5. A composition according to claim 2, at least 90% of said complexes being not greater than about 0.1 μm in particle size.

6. A composition according to claim 5, at least 90% of said complexes being about 0.004 to 0.1 μm in particle size.

7. A composition according to claim 5, at least 85% of said complexes being about 0.01 to 0.08 μm in particle size.

8. A composition according to claim 7, said reducing metal comprising a stannous reducing metal and said ligand being a diphosphonate.

9. A composition according to claim 2, said ligand being a diphosphonate.

10. A composition according to claim 2, said albumin being human serum albumin and said reducing metal being a stannous reducing metal.

11. A composition according to claim 10 stabilized with undenatured albumin and a buffer.

12. A composition according to claim 11 further comprising a non-ionic surfactant.

13. A composition according to claim 10, said composition being in the form of a freeze-dried solid.

14. A composition according to claim 10, said albumin having been denatured by application of heat at a pH differing from the apparent isoelectric point of said albumin in said composition by about 1.5 to 4 pH units.

15. A composition according to claim 14, the pH at denaturation differing from the apparent isoelectric point of said albumin by about 2 to 3.5 pH units.

16. A composition according to claim 14, said albumin having been denatured at about 80°-100° C.

17. A composition according to claim 10, said albumin having been denatured by application of heat at a pH of about 6.5 to 11.

18. A composition according to claim 17, said albumin having been denatured at a pH of about 7.5 to 9.5, and at a temperature of about 80°-100° C.

19. A composition according to claim 1, said albumin being human serum albumin, said reducing metal being a stannous reducing metal, said composition being stabilized with undenatured human serum albumin and a buffer, said complexes being denatured at a pH of about 7.5 to 9.5, and said composition being freeze-dried.

20. A radioactive imaging agent comprising $^{99m}$Tc-labelled complexes of denatured albumin and a reducing metal, at least a major portion of said complexes having a particle size of less than about 0.2 μm.

21. An agent according to claim 20 further comprising a stabilizing ligand for said reducing metal.

22. An agent according to claim 21 said albumin being human serum albumin, said reducing metal comprising a stannous reducing metal, and said ligand being selected from the group consisting of phosphonates, phosphates, aminocarboxylates, polyhydroxycarboxylates and polycarboxylates.

23. An agent according to claim 21, said ligand being a diphosphonate.

24. An agent according to claim 23, said ligand being hydroxyethylene diphosphonate.

25. An agent according to claim 23, said ligand being methylene diphosphonate.

26. An agent according to claim 21, at least 90% of said microaggregates having a particle size not greater than 0.2 μm.

27. An agent according to claim 26, at least about 85% of said complexes having a particle size of about 0.01 to 0.08 μm.

28. An agent according to claim 21, further comprising undenatured albumin, a buffer and surfactant.

29. An agent according to claim 20, said albumin being human serum albumin, said reducing metal being a stannous, reducing metal, at least 90% of said complexes having a particle size of between about 0.01 and 0.08 μm.

30. An agent according to claim 20, stabilized with undenatured human serum albumin and a buffer, said complexes being denatured at a pH differing from the apparent isoelectric point of the albumin in the composition by about 1.5 to 4 pH units.

31. An agent according to claim 30, said pH at denaturation being between about 7.5 and 9.5.

32. An agent according to claim 30, said pH at denaturation being between about 1.0 and 4.5

33. A method for making an agent for labelling with $^{99m}Tc$ for radioactive imaging, said method comprising denaturing albumin in the presence of a reducing metal to form reducing metal/denatured albumin complexes, at least the major part of said complexes having a particle size of less than about 0.2 μm.

34. A method according to claim 33, said denaturation being carried out in the presence of a stabilizing ligand for said reducing metal.

35. A method according to claim 34, said albumin being human serum albumin, said reducing metal being $Sn^{++}$ and said ligand being selected from the group consisting of a phosphonate, a phosphate, an aminocarboxylate, a polyhydroxycarboxylate and a polycarboxylate.

36. A method according to claim 35, said denaturation being carried out at a pH at which at least about 85% have a particle size between 0.01 and 0.08 μm.

37. A method according to claim 34, said denaturation being carried out at a pH at which at least 90% of the complexes have a particle size not greater than 0.2 μm.

38. A method according to claim 37, said denaturation being carried out at a pH which differs from the apparent isoelectric point of the albumin in the composition by about 1.5 to 4 pH units.

39. A method according to claim 38, said denaturation being carried out at a pH on the alkaline side of the apparent isoelectric point of said albumin.

40. A method according to claim 38, said denaturation being carried out on the acid side of the apparent isoelectric point of said albumin.

41. A method according to claim 34, said ligand being a diphosphonate.

42. A method according to claim 41, said ligand being hydroxyethylene diphosphonate.

43. A method according to claim 41, said ligand being methylene diphosphonate.

44. A method according to claim 43, said denaturation being carried out by heating at a pH of between about 7.5 and 9.5, at which at least 90% of the complexes have a particle size not greater than 0.2 μm and at least 85% have a particle size between about 0.01 and 0.08 μm, said reducing metal being a stannous reducing metal, and said albumin being human serum albumin.

45. A method according to claim 33, said denaturation being carried out by heating albumin and said reducing metal by microwave heating.

46. A method according to claim 33, said denaturation being carried out by heating albumin and said reducing metal by induction heating.

47. A method of evaluating at least one element of the reticuloendothelial system of a primate, comprising injecting into the primate a composition comprising $^{99m}Tc$ labelled reducing metal/denatured albumin complexes at least a major portion of which have a particle size of less than about 0.2 μm, to concentrate said $^{99m}Tc$-labelled complexes in the reticuloendothelial system.

48. A method according to claim 47, said composition further comprising a stabilizing ligand for said reducing metal.

49. A method according to claim 48, said reducing metal being a stannous reducing metal and said ligand being a diphosphonate.

50. A method according to claim 47, at least 90% of said complexes having a particle size not greater than 0.1 μm and at least a majority of said complexes having a particle size between 0.01 and 0.08 μm.

51. A method of imaging bone marrow in a primate, comprising injecting into the primate a composition comprising $^{99m}Tc$-labelled reducing agent/denatured albumin complexes to concentrate said $^{99m}Tc$-labelled complexes in the bone marrow.

52. The method of claim 51, wherein at least 90% of the labelled reducing agent/denatured albumin complexes have a particle size below about 0.2 μm, and the composition further comprises a stabilizing ligand for said reducing agent.

53. The method of claim 52, wherein the reducing agent is stannous, the denatured albumin is denatured human serum albumin, the stabilizing ligand is a diphosphonate, and at least 85% of the reducing agent/denatured albumin has a particle size of between about 0.01 and 0.08 μm.

54. A method of imaging at least one component of the lymphatic system in a mammal, comprising injecting into the mammal a composition comprising $^{99m}Tc$-labelled reducing agent/denatured albumin complexes to concentrate said $^{99m}Tc$-labelled complexes in the aforementioned components of the lymphatic system.

55. The method of claim 54, wherein at least 90% of the labelled reducing agent/denatured albumin complexes have a particle size below about 0.2 μm, and the composition further comprises a stabilizing ligand for said reducing metal.

56. The method of claim 55, wherein the reducing agent is stannous, the denatured albumin is denatured human serum albumin, the stabilizing ligand is a diphosphonate, and at least 85% of the reducing agent/denatured albumin has a particle size of between about 0.01 and 0.08 μm.

57. A method of evaluating the rate of clearance of particulate material from the blood of a mammal, comprising injecting into the mammal a composition comprising $^{99m}Tc$-labelled reducing agent/denatured albumin complexes, and measuring the rate of clearance of said complexes from said blood over a period of time.

58. The method of claim 57, wherein at least 90% of the labelled reducing agent/denatured albumin complexes have a particle size below about 0.2 μm, and the composition further comprises a stabilizing ligand for said reducing metal.

59. The method of claim 58, wherein the reducing agent is stannous, the denatured albumin is denatured human serum albumin, the stabilizing ligand is a diphosphonate, and at least 85% of the reducing agent/denatured albumin has a particle size of between about 0.01 and 0.08 μm.

60. A composition according to claim 1, said albumin having been denatured at a pH between about 1.0 and 4.5.

* * * * *

UNITED STATES PATENT AND TRADEMARK OFFICE
CERTIFICATE OF CORRECTION

Page 1 of 2

PATENT NO. : 4,337,240
DATED : June 29, 1982
INVENTOR(S) : Eugene L. Saklad

It is certified that error appears in the above-identified patent and that said Letters Patent is hereby corrected as shown below:

Col. 2, line 48, change "is" to ---has---;

Col. 2, line 63, insert ---in--- before "certain";

Col. 3, line 4, insert ---,--- after "buffering";

Col. 3, line 52, delete "have shown" and insert therefor ---indicate---;

Col. 4, line 18, change "and" (second occurrence) to ---the---;

Col. 5, line 19, delete "measure";

Col. 5, line 35, correct the spelling of "disappearance";

Col. 6, line 12, correct the spelling of "measurement";

Col. 7, line 54, change "inositohexaphosphate" to ---inositolhexaphosphate---;

Col. 8, line 16, change "$T^{+++}$" to ---$Ti^{+++}$---;

Col. 13, line 62, change "th" to ---the---;

Col. 14, line 46, delete "is";

UNITED STATES PATENT AND TRADEMARK OFFICE
CERTIFICATE OF CORRECTION

PATENT NO. : 4,337,240

DATED : June 29, 1982

INVENTOR(S) : Eugene L. Saklad

It is certified that error appears in the above-identified patent and that said Letters Patent is hereby corrected as shown below:

Col. 16, in Table II, change "$\geq$" to ---$>$---;

Col. 19, line 31, insert ---Sample 5--- before "Example 2".

Signed and Sealed this

Twenty-ninth Day of May 1984

[SEAL]

Attest:

GERALD J. MOSSINGHOFF

Attesting Officer — Commissioner of Patents and Trademarks